United States Patent [19]

Sun et al.

[11] 4,421,857
[45] Dec. 20, 1983

[54] NOISE CHECKING METHOD

[75] Inventors: Lilla S. Sun, Seal Beach; John C. Anderson, Burbank, both of Calif.

[73] Assignee: Beckman Instruments, Inc., Fullerton, Calif.

[21] Appl. No.: 330,973

[22] Filed: Dec. 15, 1981

[51] Int. Cl.$^3$ ................................................ G01J 3/02
[52] U.S. Cl. ...................................... 436/2; 436/110; 356/243
[58] Field of Search ............................ 436/110, 19, 2; 356/306, 319, 326, 432, 243

[56] References Cited

U.S. PATENT DOCUMENTS 3,512,895 5/1970 Grum et al. ......................... 356/243

OTHER PUBLICATIONS

JR 5, 1981, vol. 26, pp. 200-202.
Rider et al., Analytical Chemistry, vol. 18, No. 2, 1946.

*Primary Examiner*—Hiram H. Bernstein
*Attorney, Agent, or Firm*—R. J. Steinmeyer; J. E. Vanderburgh; R. S. Frieman

[57] ABSTRACT

A method for checking noise of a spectrometer or spectrophotometer. The method is of the type comprising measuring absorbance (A) or percent transmittance (%T) of a solution over a period of time. The method is characterized in that the solution comprises from about 0.040 to about 0.090 M nitrite, the nitrite being present as a nitrite ionized constituent.

10 Claims, No Drawings

NOISE CHECKING METHOD

BACKGROUND OF THE INVENTION

1. Field of the Invention

This invention relates to a method for checking the noise performance of spectrometers and spectrophotometers.

2. Description of the Prior Art

Frings et al. (1) report that the percentage of quantitative analyses performed in the clinical laboratory that involve spectrophotometry or colorimetry was estimated in 1969 to be possibly more than 95% (2). Most laboratories continue to rely heavily upon spectrometers or spectrophotometers for the majority of their analyses. Maintenance of properly functioning spectrometer and spectrophotometers is an obvious prerequisite to the assurance of accurate analytical results. Moreover, the increased regulation of clinical laboratory by governmental and professional agencies mandates that laboratory personnel periodically verify that a given spectrophotometer is functioning properly. By periodically inspecting spectrometric and spectrophotometric functions, subtle or gradual degradations in performance can be detected before they significantly affect analytical results. As a minimum, these inspections should include, inter alia, a check of noise, i.e., the random variation of signal with time.

To measure noise, one measures the absorbance (A) or percent transmittance (%T) of a solution having a broad absorption band and a maximum absorbance of about 2.0 A over a period of time.

One prior art solution employed in the past to measure noise is a potassium dichromatic solution (0.05 gm/l). This solution has an absorbance of about 2.0 A at 372 nn.

The potassium dichromatic solution possesses a relatively short shelf life, i.e., it has been observed to decrease in absorbance at a rate of about 0.02 A per month.

Accordingly, it would be very desirable to have a noise check solution which possesses all the desirable properties of the dichromatic solution and also possesses a very stable shelf life.

SUMMARY OF THE INVENTION

In accordance with the present invention, there is provided an improved method for measuring the noise of a spectrometer or spectrophotometer. More particularly, the method for checking noise is of the type comprising measuring absorbance (A) or percent transmittance (%T) of a solution over a period of time. The method of the instant invention is characterized in that the solution being measured comprises from about 0.040 to 0.090 molar nitrite, wherein the nitrite is present as a nitrite ionized constituent.

This nitrite solution, in addition to having a broad absorption band and a maximum absorbance of about 2.0 A over time, has not exhibited any decrease in absorbance over a period in excess of one year.

Still other features and attendant advantages of the present invention will become apparent to those skilled in the art from a reading of the following detailed description of the preferred embodiment.

DESCRIPTION OF THE PREFERRED EMBODIMENT

The method for verifying noise performance of the instant invention is of the type which comprises measuring the absorbance (A) or percent transmittance (%T) of a solution over a period of time. The method of the instant invention is characterized in that the solution comprises from about 0.040 to 0.090 molar nitrite, wherein the nitrite is present as a nitrite ionized constituent. Preferably, the solution employed in the method of the instant invention comprises from about 0.055 to 0.075, more preferably, from about 0.060 to about 0.070, and optimally about 0.065 molar nitrite.

Substantially any ionizable nitrite compound can be employed in the method of the instant invention. Preferably, the ionizable nitrite compound is selected from a group consisting of sodium nitrite and potassium nitrite. Optimally, the ionizable nitrite compound is sodium nitrite.

The solution employed in the method of the instant invention can be made by any convenient process known to those skilled in the art. For example, one can add a known amount of an ionizable nitrite compound to a suitable vessel. To this vessel is then added water, preferably distilled water, with mixing to dissolve the compound and thereby form a uniform solution.

The method of the instant invention for verifying noise performance of spectrometer and spectrophotometers is of the type which comprises measuring A or %T of a solution over a period of time. The method of the instant invention is characterized in that the above described solution is employed therein. The wavelength at which A or %T is measured can very depending on the particular ionizable nitrite compound employed. For example, when sodium nitrite is employed, one measures A or %T at 350 nm.

The following examples are provided for the purpose of further illustration only and are not intended to be limitations on the disclosed invention.

EXAMPLE 1

Sodium nitrite (9 gm) was placed into a two liter volumetric flask. To this flask was then added approximately two liters of distilled water. The contents of the flask were mixed well to yield a uniform solution.

EXAMPLE 2

A BECKMAN Model 42 brand spectrophotometer was turned on and allowed to warm-up to operating temperature. The wavelength was set at 350 nm. A water blank was aspirated into the spectrophotometer's flow cell and the instrument was zeroed. The water blank was removed from the instrument and the solution prepared in Example 1 was aspirated into the flow cell. The instrument read the peak-to-peak noise as per its programmed instructions and calculated the standard deviation of the noise signal. This procedure was automatically repeated three times by the instrument. The data obtained indicated that the noise signal was within acceptable limits.

Based on this disclosure, many other modifications and ramifications will naturally suggest themselves to those skilled in the art. These are intended to be comprehended as within the scope of this invention.

BIBLIOGRAPHY

1. Frings et al., *Clin. Chem.*, 25(6):1013–1017 (1979).

2. Rand, *Clin. Chem.*, 15:839–863 (1969).

The embodiments of the invention in which an exclusive property or privilege is claimed are defined as follows:

1. In a method for checking noise of an optical instrument, said instrument being capable of measuring an absorption property of a material as a function of wavelength, of the type comprising measuring an absorption property of a solution over a period of time, the improvement comprising employing as said solution one comprising from about 0.040 to 0.090 molar nitrite, wherein said nitrite is present as a nitrite ionized constituent.

2. The method of claim 1 wherein said solution comprises from about 0.055 to about 0.075 molar nitrite.

3. The method of claim 1 wherein said solution comprises from about 0.060 to about 0.070 molar nitrte.

4. The method of any one of claims 1, 2 or 3 wherein said nitrite ionized constituent is selected from a group consisting of sodium nitrite and potassium nitrite.

5. The method of any one of claims 1, 2 or 3 wherein said nitrite ionized constituent is sodium nitrite.

6. The method of claim 1 wherein said solution comprises 0.065 molar sodium nitrite and said measurement is made at about 350 nm.

7. The method of claim 1 wherein said optical instrument is a spectrometer and said absorption property is absorbance (A).

8. The method of claim 1 wherein said optical instrument is a spectrometer and said absorption property is percent transmittance (%T).

9. The method of claim 1 wherein said optical instrument is a spectrophotometer and said absorption property is absorbance (A).

10. The method of claim 1 wherein said optical instrument is a spectrophotometer and said absorption property is percent transmittance (%T).

* * * * *